United States Patent [19]

Amey

[11] 4,091,674
[45] May 30, 1978

[54] AIR SAMPLING PUMP

[76] Inventor: Guy C. Amey, P.O. Box 133, Arkansas City, Kans. 67005

[21] Appl. No.: 694,109

[22] Filed: Jun. 9, 1976

[51] Int. Cl.² .............................................. G01N 1/24
[52] U.S. Cl. ................................... 73/421.5 R; 73/23
[58] Field of Search ........................ 73/421.5 R, 23, 28

[56] References Cited

U.S. PATENT DOCUMENTS

| 2,489,654 | 11/1949 | Main-Smith et al. ...... 73/421.5 R X |
| 3,093,001 | 6/1963 | Williams .......................... 73/421.5 R |
| 3,238,783 | 3/1966 | Wright ............................. 73/421.5 R |
| 3,782,198 | 1/1974 | Wächter et al. ................. 73/421.5 R |
| 3,953,152 | 4/1976 | Sipin ......................................... 417/45 |

Primary Examiner—Charles A. Ruehl
Attorney, Agent, or Firm—Head, Johnson & Chafin

[57] ABSTRACT

An electronically timed, positive displacement air sampling pump for use with a wide variety of air sample collecting devices and in a wide range of environmental conditions. The invention provides for accurate average flow rate, independently metered total volume, operating time register and audible "rate fault" alarm.

8 Claims, 4 Drawing Figures

AIR SAMPLING PUMP

BACKGROUND

This invention is in the field of environmental air sampling and air monitoring where an electrically powered air pump is required. The accuracy and reliability of the air sampling pump is a major consideration since it affects the accuracy of the air contaminant measurement. Pumps of this type need to be made small and battery operated for portability so that they may be used in applications such as personal air exposure monitoring. Air sampling pumps are commonly used to draw air through collecting devices, which are designed to trap the contaminants in the air within the device and store same for later analysis. When analyzing the contaminants trapped in the collector device, the total volume of air that passed through the device during monitoring must be known. The average flow rate of the air through the device during monitoring must also be constant over the monitoring period.

There are two basic types of air sampling pumps. One which is a high flow rate pump in the range of one (1) to three (3) liters per minute which is used for collection of particulate matter in air. The other type pump is a low flow rate pump in the range of 1 to 300 ml./minute which is used for the collection of chemical compounds present in the air.

Most standards today, for the measurement of personnel exposure to hazardous/toxic vapors, are specified in terms of time weighted average (TWA). The TWA exposure to a compound is the average concentration of that compound over a specified period of elapsed time as measured in the breathing zone of an individual. In the industrial hygiene field, the TWA exposure is the common parameter and is normally specified for a period of 8 hours. Additional specifications, such as average exposure over a fifteen minute maximum period and absolute peak levels, are also sometimes specified. The 8 hour TWA is related to an employee's exposure during a normal work day and is considered to be the most meaningful method of assessing his exposure to a potentially hazardous vapor environment.

Peak exposures must be measured with a continuous measuring instrument. Fifteen minute TWA exposures can be measured by either averaging continuous readings or with an integrating method such as a sample collection bag or sample collecting tube. Accurate measurement of the 8 hour TWA is most readily accomplished using a full-period (continuous) sampling through a collector tube, wherein the compounds in the air are trapped in a sorbent material. The sorbent material is contained in a tube through which the air is drawn at a constant rate during the full 8 hour period of concern. Periodic sampling, to arrive at an estimated eight hour TWA, can also be used; however, the results must be factored to arrive at a statistical lower confidence level (LCL) which must be reported with the data.

In recent years, many portable air sampling pumps have been introduced for pumping air through collector tubes as a means of obtaining samples for the determination of TWA exposure. As the methodology has developed, it has become increasingly apparent that the performance of the sample pump is very critical to the accuracy of the air contaminant measurement.

Sampling pumps for time-weighted average (TWA) measurements must maintain a constant flow rate, even if provisions are made for determining the total volume pumped. Any pump can have a flow rate malfunction, due to changes in flow restriction as well as other factors, i.e., every air pump malfunctions when the input line is blocked. The possibility of a fault cannot be eliminated.

An error in the value of "total volume pumped" produces a like error in the time-weighted average (TWA) measurement variations in sample flow rate produces less pronounced error in the TWA measurement but cannot be compensated for without knowledge of flow rate and contamination level as a function of time. If no independent means is provided for measuring the total volume pumped, this value is calculated from flow rate and becomes dependent on the flow rate accuracy. The total operating time of a pump must be known to calculate total volume from flow rate, i.e., total volume = time X flow rate. If a pump stops or is turned off for an unknown period during monitoring, the total volume will be unknown.

There are many air sampling pumps on the market for use in drawing air samples through chemical trapping collector tubes. These existing pumps use a variety of methods for accomplishing their task of pumping air at a constant average rate over a period of time in a fashion such that the total volume of air through the collection device is known at the end of the air monitoring period. The most common type pump is a standard motor driven diaphragm pump which operates through a gear reduction train such that the speed of the diaphragm pump can be varied to establish the flow rate of air through a given air collection device. In application the restriction to air flow and resulting pressure drop across a collector tube can vary as function of time, as can the speed of the motor driven diaphragm pump due to variations in the supply voltage to the motor. These type variations can cause variations in the air flow rate through the collection device which would make it impossible to arrive at an accurate measurement of total volume of air through the collector during the monitoring period.

Pumps are available which incorporate an air flow sensor which is used to sense the rate of air flow through the pump and servo a signal back to the pump motor to control its speed such that it maintains a constant flow rate during the monitoring period. Other type air sampling pumps measure the total volume of air pumped through the collection device by counting the strokes of a diaphragm or bellows type pump which simulates a measurement of positive air displacement. Of the many pumps available today, none are capable of providing a constant average flow rate with varying restrictions in the pumping line, while also independently measuring the volume of air displaced through the pump as related to ambient pressure air, while also providing a register of total pump operating time, and also providing a means for audible or visual alarm in the event the flow rate changes outside its specified limits.

SUMMARY

The invention involves a new and unique method of pumping air at low flow rates through chemical collecting devices in such a way as to provide an accurate measurement of the time-weighted average (TWA) of the chemical concentration in the air sample during the period of monitoring.

The invention is a portable, battery-operated air sampling pump for personnel and area environmental air monitoring which can be used with a variety of air sample collecting devices. It can be utilized in a wide range of indoor or outdoor environmental conditions. The invention provides for accurate average flow rate, reliable performance, measured volume, metered operating time, audible "rate fault" alarm and low cost.

The pump operates on the principle of timed positive displacement bellows strokes with a pressure switch to assure true air displacement. The preset flow rate is maintained over a wide range of collector tube restrictions and an audible flow rate failure alarm is incorporated. A mechanical stroke counter is included to measure "operating" time of the pump as well as accurately verify total volume of air pumped.

The pump may be powered from batteries of A.C. power and can be packaged in less than 40 cubic inches volume with a weight of less than 20 ounces.

The pump operates on the principle of positive displacement of air. A bellows is used to measure the constant volume of the displacement and also function as a pressure switch to ensure the air displaced has a fixed relationship to volume at ambient pressure. In addition, this fixed volume of air is pumped repeatedly at a preset frequency to maintain a constant average pumping rate and the total volume is independently metered by counting pump strokes.

In operation, an electronic timing circuit in the pump generates a pulse at a preset frequency (adjustable) to obtain the desired flow rate. This pulse starts a pumping cycle which consists of turning on a diaphragm pump which draws air through the collection device and exhausts the same air into the REGISTER bellows. Immediately after the pump is turned on, the vacuum on the input side of the pump is utilized to pneumatically actuate and close an exhaust valve on the bellows. The REGISTER bellows expands against a spring load until a REGISTER limit switch is actuated, shutting off the pump. The pressure inside the bellows when the limit switch actuates will be constant and is established by the spring load.

When the pump is turned off, the vacuum at its input side decays and the exhaust valve on the bellows opens allowing the bellows to collapse. A positive stop determines the minimum bellows expansion and a SET limit switch is actuated immediately prior to reaching this stop. The bellows then stays at rest until the next cycle is initiated with a timing pulse. An arrangement of check and pneumatic valving eliminates error in the volume measurement that could result from leakage of the bellows exhaust valve.

DETAILED DESCRIPTION OF THE DRAWINGS

DETAILED DESCRIPTION

Before explaining the present invention in detail, it is to be understood that the invention is not to be limited in its application to the details of construction and the arrangement of parts illustrated in the accompanying drawings, since the invention is capable of other embodiments and of being practiced or carried out in various ways. Also, it is to be understood that the phraseology or terminology employed herein is for the purpose of description and not of limitation.

Figure 1:
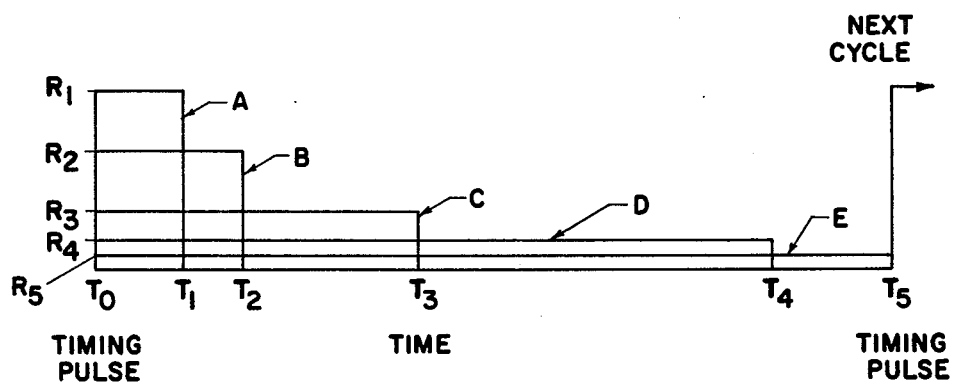
FIG. 1 is a graphic display of the functions of the pump of the invention.

To illustrate the functions which take place to complete a pumping cycle see curve A of FIG. 1.

1. A timing impulse turns on the diaphragm pump at $T_0$ and the bellows exhaust valve is pneumatically closed. Air is drawn through the collection device and exhausted into the bellows.
2. The bellows expand under pressure against a spring load until the REGISTER limit switch is actuated at time $T_1$.
3. The pump is turned off and the bellows exhaust valve opened. The spring then collapses the bellows to their original positive stop. A SET limit switch is closed just prior to the bellows reaching its stop.
4. In the period between $T_1$ and the next timing pulse, the pump and bellows are at rest.

The period between $T_0$ and $T_1$ will vary inversely with the flow rate through the collection device during the period the pump is on.

Curve B illustrates a pump cycle with a higher restriction and subsequently lower flow rate and Curve C an even higher restriction. Curve D illustrates the cycle with the maximum restrictive load that can be pumped against without a fault indication ($T_4$ to $T_0$ is reset time). Curve E is a cycle in which the next timing pulse was introduced before the fixed volume of air could be pumped and the bellows reset actuating the SET limit switch.

The logic and control circuitry in the pump is such that the SET limit switch must be activated when a timing pulse is introduced, otherwise an audible "rate fault" alarm is energized. The audible alarm will stay on continually if there is a complete restriction or will automatically be reset when the REGISTER limit switch actuates.

The pump, in effect, maintains a constant average flow rate by automatically adjusting the pumping duty cycle. Flow restrictions designed into the pump limit the minimum duty cycle. The maximum duty cycle is established by the maximum restriction that can be pumped prior to a fault alarm indication. A mechanical counter is incorporated in the pump to meter the bellows strokes, providing an independent measurement of total volumed pumped. In addition, the counter provides a measurement of total operating time since the frequency of the strokes is preset.

Figure 2:
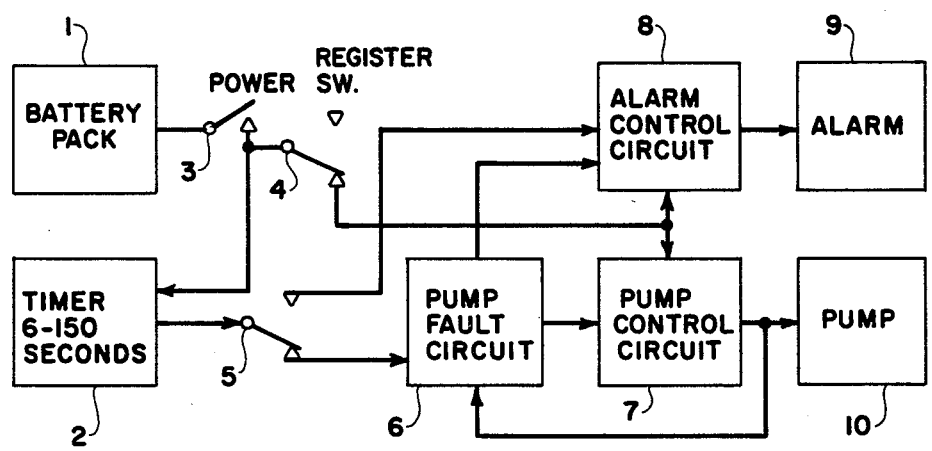
FIG. 2 is a block diagram of the pump indicating the various interrelationships of the pump circuits.

Referring now to FIG. 2 the apparatus of this invention generally includes a battery pack at 1, an electronic timing pulse circuit at 2, a power on-off switch at 3, a REGISTER limit type switch at 4, a SET limit type switch at 5, a pump fault circuit at 6, a pump control circuit at 7, an alarm control circuit at 8, an audible alarm device at 9 and a motor driven diaphragm type pump at 10.

The battery pack 1 provides power for operation of the pump 10 (which can be any type, preferably a diaphragm type), the electronics and the alarm circuit when the power switch 3 is closed. The electronic timing pulse circuit 2 is preset with a potentiometer to provide a pulse out at a given frequency depending on the desired average flow rate of the pump. Mechanical limit switches 4 and 5 are shown in their normal position at the beginning of a pumping cycle. When a pulse is sent out from 2 through switch 5, it is normally passed through the pump fault circuit 6 and goes into the pump control circuit 7. The introduction of the start pulse in 7 turns on a solid state switch which provides power from the battery pack 1 through the power switch 3 then through REGISTER switch 4 to the pump 10 which turns the diaphragm pump on. The diaphragm pump 10 pumps air through the collection device until the pump bellows mechanism forces the mechanical limit switch 4 to open, removing power from the pump control circuit 7 which subsequently removes power from the pump 10. When the pump 10 initially starts expanding the REGISTER bellows, the SET limit switch 5 is mechanically moved to its opposite position with the wiper going to the contact from 8. When the pump 10 is turned off and the pressure on the input side of the pump increases towards ambient, the pneumatically operated exhaust valve is opened allowing air to leave the REGISTER bellows causing the bellows to collapse under the spring load to their original fixed stop position. As the bellows start to collapse, REGISTER switch 4 goes back to its original position and the SET limit switch 5 is returned to its original position just prior to the bellows reaching their positive stop. If all the described conditions have taken place and the bellows has pumped the volume of air established by its limits in the time period prior to the generation of the next timing pulse, the cycle will repeat itself. However, if the limit SET switch 5 is not returned to its original position at the time the next timing pulse originates from 2, the timing pulse is sent through the alternate contacts of 5 to the alarm control circuit 8 which turns on power to an audible alarm 9. The alarm will remain on until such time as the SET limit switch 5 is reset to its original position. The pump fault circuit 6 will send the timing pulse to the alarm control circuit 8 to turn on the alarm 9 if the limit switch 5 is in its normal SET position and the pump motor is running at the time the timing pulse is generated. This circuit is to protect against a condition wherein the pump is turned on in its normal fashion but never moves the bellows off its positive stops causing SET switch 5 to open. This fault could be caused by a problem such as a faulty exhaust valve, a leak in the air system or a mechanical problem in the pump itself.

The timing pulse circuit can be any suitable electronic timing circuit such as a simple unijunction relaxation oscillator which will put out a pulse at a preset frequency which can be varied by changing a resistor or capacitor. Limit switches 4 and 5 can be standard micro switches which are actuated mechanically by a positioning device. The pump fault circuit is an arrangement of semiconductors which sense the presence of current going to the pump motor and uses this current indication to direct the timing pulse to the alarm control circuit 8 rather than to the pump control circuit 7 which would be the normal condition. The alarm control circuit 8 and pump control circuit 7 can be standard silicon control rectifier (SCR) circuits which are turned on and stay on until power is removed from the circuit. The alarm 9 can be any suitable audible alarm device such as a buzzer. The diaphragm pump 10 is any suitable electrically motor driven diaphragm pump of the type in common use.

Figure 3:
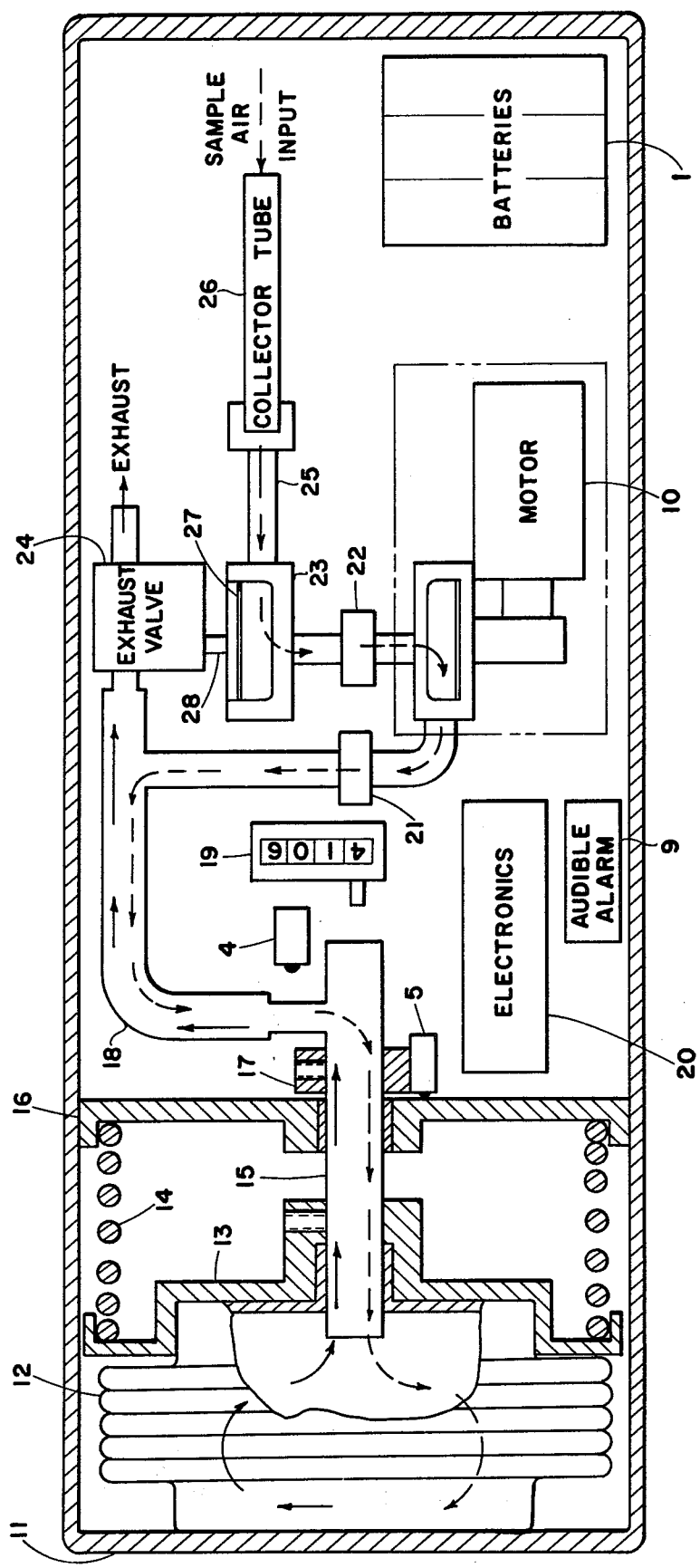
FIG. 3 is a functional diagram of the pump showing the air flow paths and mechanisms within the pump.
Figure 4:
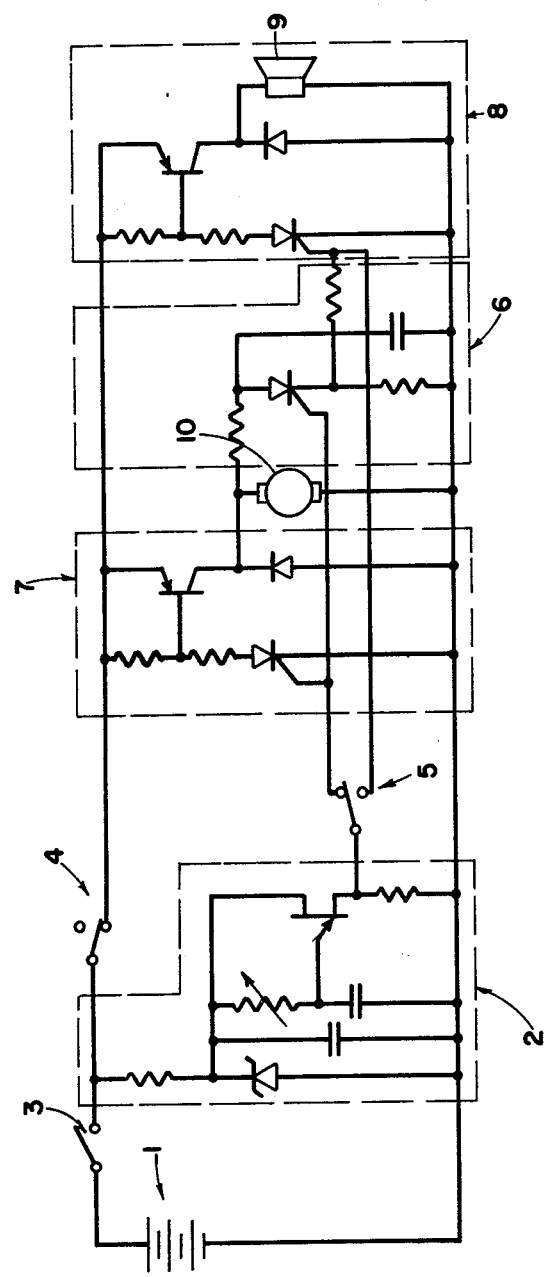
FIG. 4 is a detailed electrical circuit diagram.

FIG. 3 is a functional diagram of the invention illustrating the pumping and metering mechanics and the sample and exhaust air flow. FIG. 3 illustrates the configuration of the REGISTER bellows under normal conditions prior to generation of a timing pulse to start a normal pumping cycle. Plates 11 and 16 are fixed mechanically to each other and define a space between them which encloses the REGISTER bellows 12. The Register bellows is loaded against end plate 11 by plate 13 and plate 13 is biased by coil spring 14 interposed between plate 13 and a plate 16. The maximum distance that REGISTER bellows 12 can be collapsed by spring 14 is limited by the positive mechanical stop 17 which is attached to tube 15 which is mechanically attached to plate 13. In the position shown, the REGISTER bellows 12 are at rest waiting for the start of a pumping cycle. When a timing pulse is generated, it turns on the motor driven diaphragm pump 10. The diaphragm pump 10 draws sample air through the collector tube 26 via tube 25 through the exhaust valve body 23 and then through the pump input check valve 22 to the diaphragm pump cavity. Immediately upon drawing air through collector tube 26 a negative pressure is created in tube 25 and the input side of exhaust valve body 23. This negative pressure creates a force on diaphragm 27 which pulls a valve stem 28 down, closing off the exhaust path through exhaust port 29. The air being exhausted from the diaphragm pump 10 through exhaust check valve 21 is routed past the closed exhaust valve 24 through tube 18 and tube 15 and into the REGISTER bellows 12. This exhaust air from the pump 10 causes the REGISTER bellows 12 to expand within the cavity between plates 11 and 16 and compress coil spring 14. The expanding bellows also causes tube 15 to move in a bushing in plate 16 which, under initial travel, moves SET limit switch 5 from plate 16 causing switch 5 to go to its alarm position. Exhaust air is pumped into REGISTER bellows 12 to expand the bellows to the point where positive stop 17 on tube 15 reaches and actuates REGISTER limit switch 4 which causes the diaphragm pump to stop pumping. Because the REGISTER bellows 12 are being expanded against a coil spring 14, the pressure inside the bellows 12 at the time the positive stop 17 actuates limit switch 4 is constant for each stroke; it essentially acts as a pressure switch. Prior to stop 17 actuating limit switch 4, tube 15 actuates a suitable mechanical counter such as any well-known ratchet resettable type or light emitting diode type as indicated at 19 such that when tube 15 retracts the next sequential number is rotated up on the counter 19. When the REGISTER limit switch 4 is actuated and the diaphragm pump turned off, the negative pressure in valve block 23 goes to ambient pressure by drawing additional air through collector tube 26. As the pressure in valve block 23 approaches ambient, the force on diaphragm 27 is reduced and allows valve stem 28 to retract. This opens exhaust valve 24 providing an air path between tube 18 and exhaust port 29. This allows the air under compression in REGISTER bellows 12 to immediately exhaust via tube 15 and tube 18 through the now open exhaust valve 24 and out through exhaust port 29. The REGISTER bellows 12 then collapse to their original position under the load of spring 14 until such time as positive stop 17 hits plate 16. As the bellows start to collapse, the limit switch 4 is deactivated enabling the pump or motor control circuit to turn the pump 10 on again when the timed start pulse is fed to the motor-pump control circuit 7. As the bellows collapse, the shaft for actuating the mechanical stroke counter retracts causing the mechanical counter to reset and await another pump stroke actuation. Just prior the bellows 12 returning to its original positive mechanical stops, the set limit switch 5 is reactivated switching its contacts from the alarm actuating position to the pump ready position. At the end of this phase of the pumping cycle, the bellows remains at rest until another motor-pump cycle start pulse is generated and sent from the electronic timing pulse circuit 2.

The pumping cycle described will repeat itself with each timing pulse unless the flow restrictive load that it is pumping against becomes greater than the pumping capacity of the pump or if there is a malfunction within the pump apparatus itself. Provisions for providing an immediate indication are included in the event that the pump cannot maintain its preset average pumping flow rate. If the flow restriction is sufficiently high such that the pump cannot complete a full pumping cycle between the timing pulses, or such that the bellows returns to its original fixed stop position causing the set limit switch 5 to switch from the alarm actuate position to the pump ready position, the next timing pulse is sent to the alarm control circuit rather than to the motor pump control circuit which would be its normal path. A pulse received by the alarm control circuit turns on an audible or visual alarm which will remain on until the set limit switch 5 is reactivated or the apparatus power is turned off.

What is claimed is:

1. An air-sampling pump system for drawing air through a collection device, comprising:
   an electric motor driven air pump having an inlet and outlet,
   an inlet passageway,
   means for sealably connecting the inlet passageway in series with the collection device,
   a normally collapsed bellows, an outlet passageway sealably connecting the outlet of said pump with the interior of the bellows,
   electrical power supply and timing pulse circuit means to start, at pre-set frequency, said electric motor and pump,
   first switch means operable upon said bellows reaching desired expanded condition to stop said electric motor and said pumping cycle;
   second switch means operable
   (1) on collapse of said bellows to close a motor-pump control circuit and allow said electric motor to receive said timing pulse, and
   (2) on initial movement of said bellows to open said control circuit such that upon failure of said bellows to reach said expanded condition, said timing pulse is directed to activate an alarm circuit;
   valve means connected to said outlet passageway and operable to an open position to exhaust said outlet passageway and permit said bellows to collapse and to a closed position, at the start of said pump, to permit said bellows to expand; and
   counter means to indicate the number of times said bellows has reached said expanded condition.

2. A system of claim 1 wherein said valve means is operated to close by reduced pressure from the inlet passageway.

3. A system of claim 1 including check valve means in said inlet passageway and in said outlet passageway, said check valve means open during flow of sample air and closed when said valve exhausts said outlet passageway.

4. A system of claim 1 wherein said second switch is also operable, upon failure of said bellows to move, to shut off further timing pulses to said motor yet allow said alarm circuit to function.

5. A system of claim 1 wherein said pump is a diaphragm pump.

6. A system of claim 1 wherein said alarm circuit is audible and/or visual.

7. A system of claim 1 wherein said counter is a ratchet-resettable type.

8. A system of claim 1 wherein said counter is a light emitting diode type.

* * * * *